United States Patent
Susel et al.

(10) Patent No.: US 9,208,671 B2
(45) Date of Patent: Dec. 8, 2015

(54) REDUNDANT INPUT PIPE NETWORKS IN ASPIRATED SMOKE DETECTORS

(71) Applicant: Honeywell Intrnational Inc., Morristown, NJ (US)

(72) Inventors: Michele Susel, Trieste (IT); Federico Cernoia, Udine (IT)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 91 days.

(21) Appl. No.: 14/097,564

(22) Filed: Dec. 5, 2013

(65) Prior Publication Data

US 2015/0161865 A1    Jun. 11, 2015

(51) Int. Cl.

| G08B 23/00 | (2006.01) |
|---|---|
| B08B 17/00 | (2006.01) |
| H02B 1/00 | (2006.01) |
| F21S 8/04 | (2006.01) |
| A62C 3/16 | (2006.01) |
| G08B 17/10 | (2006.01) |
| G01N 1/26 | (2006.01) |
| G08B 29/16 | (2006.01) |
| G01N 1/24 | (2006.01) |

(52) U.S. Cl.
CPC  G08B 17/10 (2013.01); G01N 1/26 (2013.01); G08B 29/16 (2013.01); F21S 8/04 (2013.01); *G01N 2001/245* (2013.01)

(58) Field of Classification Search
CPC ........ F21S 8/04; F21V 33/0076; F21V 29/15; G08B 17/10; G08B 17/12; F21Y 2105/00; A62C 3/16; H02B 1/565; G01F 7/00

USPC ................... 340/693.5, 628, 577, 693.6, 632; 361/600

See application file for complete search history.

(56) References Cited

U.S. PATENT DOCUMENTS

| 5,221,292 | A  * | 6/1993 | Aoyama ........................ 96/142 |
|---|---|---|---|
| 6,672,255 | B1 * | 1/2004 | Zayas ............................ 122/7 R |
| 8,629,780 | B2 * | 1/2014 | Goulet et al. ................. 340/632 |
| 2003/0063007 | A1* | 4/2003 | Seelbach et al. ............. 340/628 |
| 2003/0182998 | A1* | 10/2003 | Goto et al. ................. 73/204.21 |
| 2005/0040252 | A1* | 2/2005 | Thomann et al. ............. 239/302 |
| 2005/0178539 | A1* | 8/2005 | Rotta et al. ................... 165/235 |

(Continued)

FOREIGN PATENT DOCUMENTS

| EP | 1 811 478 A1 | 7/2007 |
|---|---|---|
| WO | WO 2005/048207 A1 | 5/2005 |

(Continued)

OTHER PUBLICATIONS extended European search report for corresponding EP application 14193553.6, dated Apr. 30, 2015.

*Primary Examiner* — Fekadeselassie Girma
(74) *Attorney, Agent, or Firm* — Husch Blackwell LLP

(57) ABSTRACT

An aspirated detecting system includes a multi-channel aspirated smoke detector with each channel including an air moving element, such as a fan, first and second sets of substantially identical air flow pipes where each set defines a plurality of spaced apart inflow ports. Control circuits activate a first element and then a second element to establish a transport time associated with at least one inflow port in response to the detector sensing a predetermined smoke condition. The control circuits include a storage unit which includes pre-stored timer values which are associated with respective transport times from an associated inflow port.

19 Claims, 4 Drawing Sheets

ASD,MPN and RPN status during normal operations

(56) References Cited

U.S. PATENT DOCUMENTS

| | | |
|---|---|---|
| 2007/0008157 A1* | 1/2007 | Siemens et al. ............... 340/577 |
| 2009/0253364 A1* | 10/2009 | Henry ........................... 454/229 |
| 2010/0089240 A1* | 4/2010 | Krichtafovitch ................. 96/32 |
| 2010/0263882 A1* | 10/2010 | Bodemann ..................... 169/17 |
| 2010/0300357 A1* | 12/2010 | Yamamoto et al. ....... 118/723 E |
| 2011/0050433 A1* | 3/2011 | Luterotti ....................... 340/628 |
| 2012/0079871 A1* | 4/2012 | Williamson ................. 73/28.01 |
| 2012/0227929 A1* | 9/2012 | Rose et al. .................. 165/11.1 |
| 2012/0319853 A1* | 12/2012 | Goulet et al. ................. 340/632 |
| 2013/0061659 A1* | 3/2013 | Ajay et al. ................... 73/28.04 |
| 2014/0015678 A1* | 1/2014 | Zribi et al. ................... 340/589 |
| 2014/0049400 A1* | 2/2014 | Holzer ....................... 340/693.5 |
| 2014/0190198 A1* | 7/2014 | Slessman et al. .............. 62/314 |
| 2014/0318888 A1* | 10/2014 | Kess et al. .................... 181/228 |
| 2015/0112323 A1* | 4/2015 | Hagg ............................. 606/34 |

FOREIGN PATENT DOCUMENTS

| | | |
|---|---|---|
| WO | WO 2007/028939 A1 | 3/2007 |
| WO | WO 2009/149978 A1 | 12/2009 |

* cited by examiner

ASD, MPN and RPN status after the pipe network installation

ASD, MPN and RPN status during normal operations

ASD, MPN and RPN status when a fire event starts at time 0

ASD, MPN and RPN status when a fire is detected by MCH at time Tt

ASD, MPN and RPN status when a fire is detected by RCH at time 2*Tt

Computer and software-based calculation of transport times Ttx

On site testing-based measurements of transport times TTx

REDUNDANT INPUT PIPE NETWORKS IN ASPIRATED SMOKE DETECTORS

FIELD

The application pertains to aspirated smoke detectors. More particularly, the application pertains to such detectors wherein a redundant set of intake pipes is provided to determine the location of the sampling point into which smoke is flowing.

BACKGROUND

An aspirating smoke detector is a fire detection system composed of an aspirated smoke detector (ASD) and a pipe network. A fan inside the detector draws the air from the pipe. It is very common to find on the market devices with two (or more) channels and two (or more) fans, completely independent one from the other. In order to draw air and eventually smoke inside the detector, the pipe has to be properly drilled.

Every drilled opening in the pipe is a sampling point. For example, a sampling point can cover a single room. In this way, if the fire system should protect ten rooms, ten holes, or sample points, have to be present in the pipe network. It is well known that with an aspiration detector it is difficult to detect in a reliable way from which hole smoke has enter. In other words, considering the ten room example above, it is difficult to detect the room where the fire has developed.

In the prior art, it is known that a way to detect the active smoke sample hole or sample point (SSH), is to use a secondary fan inside the detector. This fan rotates in the opposite direction with respect to the main fan.

In brief, when the ASD indicates an alarm, the main fan is stopped and a secondary fan is turned on, and rotates in the opposite direction. The combination of air and smoke that caused the alarm would be eliminated from the pipe such that only clean air, without smoke, is present in the pipe. At this time, a timer is triggered inside the device and the fans return to normal operation (main fan running, aspirating smoke, secondary fan stopped). Air and smoke are introduced again into the pipe: when smoke is detected, the timer is stopped. By comparing this time interval with the transport time of all the holes in the pipe network, the SSH can be determined.

DETAILED DESCRIPTION

Figure 1:
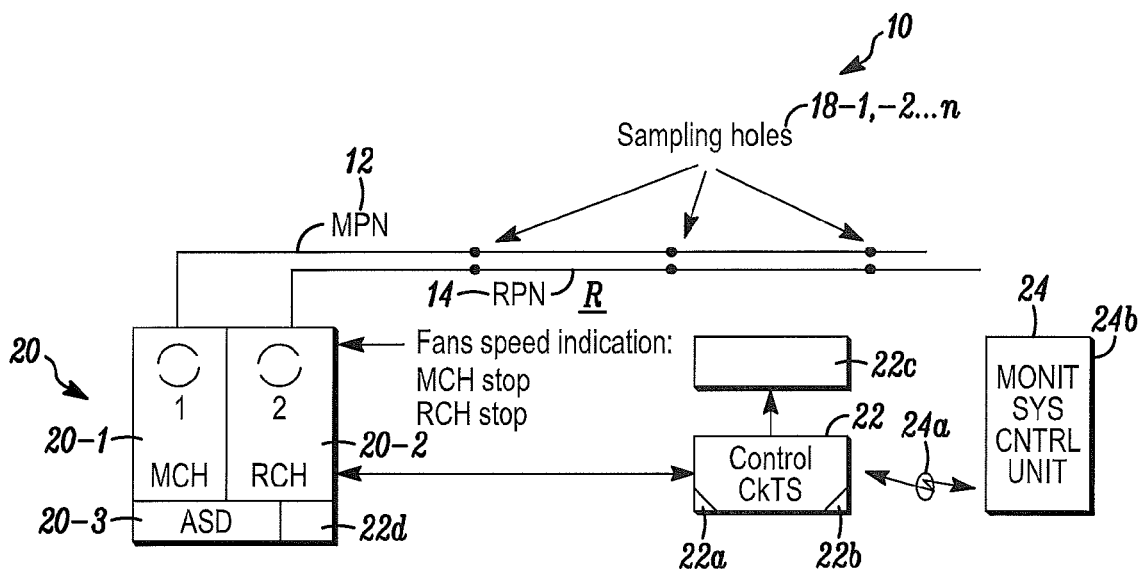
FIG. 1 is a block diagram of an embodiment hereof before operation.

While disclosed embodiments can take many different forms, specific embodiments hereof are shown in the drawings and will be described herein in detail with the understanding that the present disclosure is to be considered as an exemplification of the principles hereof, as well as the best mode of practicing same, and is not intended to limit the claims hereof to the specific embodiment illustrated.

In accordance herewith, a redundant system is able to detect with precision the sampling point, or hole (SSH smoke sampling hole), where smoke, is entering the main intake pipe system. This result is achieved by implementation of a redundant pipe network adjacent to the main pipe system, and having substantially the same design (number of holes, dimensions and so on). In view of the redundancy of the pipe networks, the aspirated smoke detector (ASD) has primary and redundant smoke sensing chambers. Each chamber has an independently controllable fan, ventilator, or blower, to provide an inflow of any smoke at a smoke sensing point. Moreover, the fan speed of the each of the fans, or ventilators in the ASD is synchronized as described below.

Embodiments hereof provide a two-way system to facilitate the recognition of the smoke received at a sample point. A pre-calculated software table and/or an on-site calibration table can also be provided. Furthermore, a visual and/or audible output device can also be provided to present an indication of the active sample point to the user. In this way an appropriate fire fighting decision can be made.

Unlike the prior art, embodiments hereof introduce a redundant pipe system to redundantly determine the location of an active smoke sampling point using unidirectional fans, and without a need for an intervening smoke elimination process. Moreover, and unlike embodiments hereof, in the prior art it is necessary to use two fans alternatively rotating in opposite directions.

In another aspect hereof, advantageously, the active sample point can be determined without using the normal/revert/normal sequence of fan operation disclosed in the prior art. In yet another aspect, fans need only rotate in one direction to identify an active sample point, and the prior art cleaning process is not needed. In this way, the time required for active sample point location identification is reduced. Moreover, the fan control systems (hardware control and firmware processes) can be simpler and less costly in part because of the hardware already present in multi-channel detectors.

During pipe network installation, a redundant pipe network (RPN) is installed close to the main pipe network (MPN). The RPN has to be made of the same materials, with substantially the same geometric details as the MPN—e.g. internal pipe diameter, bends, joints, holes distance and diameters. The two channels of the ASD are coupled to the two pipe intake networks.

Those of skill will understand that various types of multi-channel detectors can be used. All such variations come within the spirit and scope hereof.

MPN has to be built to transport air in the main channel MCH, while RPN transports air in the redundant channel RCH. This phase is presented in FIG. 1, including the ASD, MPN, RPN and sampling holes.

An aspirated smoke detector system 10 is illustrated in FIGS. 1-5 illustrating various aspects of a process of determining which smoke sample point is active. System 10 is illustrated as installed in a region R, which might have a plurality of sub-sections. System 10 includes a main pipe network 12 and a substantially similar redundant pipe network 14 which is installed throughout the region R to provide smoke from a plurality of smoke sample points 18 formed in pipe networks 12, 14. The access points 18 for each of the networks 12, 14 are substantially identical.

System 10 also includes a multi-channel aspirated smoke detector unit 20. Unit 20 includes fan or blowers, along with speed control circuitry 20-1, 20-2. The elements 20-1, -2 are in turn coupled to aspirated smoke, or gas, detector 20-3. None of the details of the elements 20-1, -2 or detector 20-3 are limitations hereof except to the extent described herein.

System 10 includes control circuits 22 which can be implemented in part as a programmable processor 22a, and associated control software 22b. The control circuits are coupled to a visual or audible output device 22c which can provide a local output as to smoke or gas levels. Control circuits 22 can be coupled to unit 20 so as to control the fans 20-1, -2 and to receive ambient condition outputs such as smoke or gas levels from the detector 20-3.

As described in more detail subsequently, a storage unit 22d, in either detector 20-3 or circuits 22 can be provided to store transport times associated with the sample points 18. Storage unit 22d can be implement with a variety of technologies without departing from the spirit and scope hereof.

Circuits 22 can be coupled wired or wirelessly via a medium 24a to a displaced monitoring system control unit 24. Unit 24 can include a visual output device 24 to present information as to region R to a user.

Figure 2:
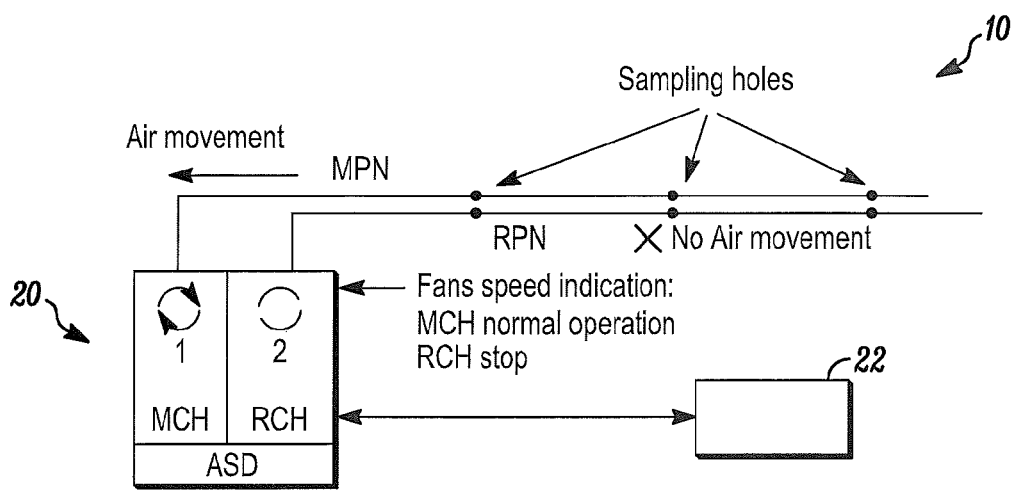
FIG. 2 is a block diagram of the embodiment of FIG. 1 when in normal operation.

FIG. 2 illustrates normal ASD operation. The MCH 20-1 fan is always working and aspirating air. The RCH fan 20-2 is not working, and so it is not aspirating air.

Figure 3:
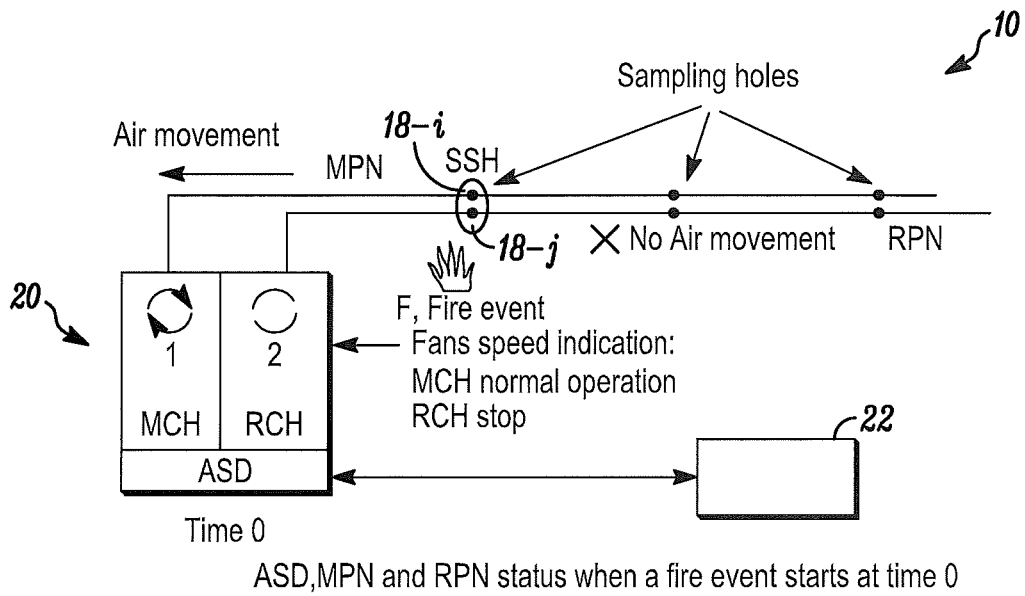
FIG. 3 is a block diagram of the embodiment of FIG. 1 in the presence of a fire event.

At any time, a fire can develop; let's call this time instant as time 0. As a consequence of a fire event F, smoke enters a sampling hole 18-i of the MPN 12. This condition is illustrated in FIG. 3.

Smoke that has entered main pipe network 12 travels, for a transport time, to the unit 20. After the transport time of the smoke from the sampling point 18-i to the ASD 20-3, here called Tt, the ASD, in conjunction with control circuits 22, indicates an alarm due to smoke sensed from the MCH 20-1. Note that the smoke travels only in the main pipes MPN 12, because secondary fan 20-2 is stopped. As a consequence, only smoke that reaches MCH 20-1 indicates an alarm condition. The transport time is unknown.

The transport time, as is known, is defined as the time required for the smoke to travel from the sampling holes, such as 18-i, to the ASD. The transport time includes also the processing time of the sensor 20-3 and control circuits 22 to indicate the alarm. However, this doesn't affect any consideration or add any limitation to the determination of the location of sample point 18-i as those of skill will understand from reading this disclosure.

Figure 4:
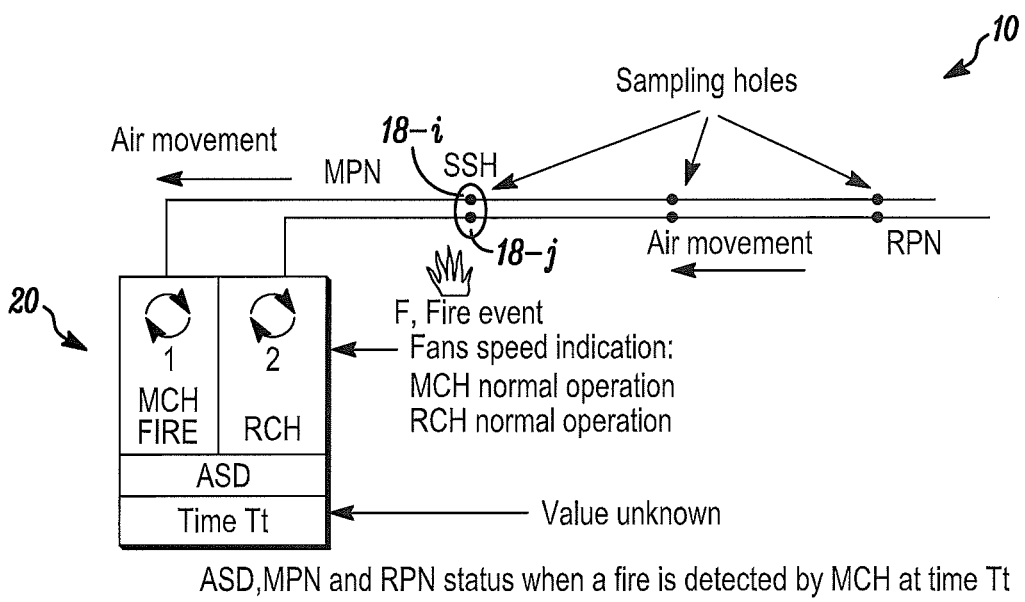
FIG. 4 is a block diagram of the embodiment of FIG. 3 when the fire event is detected by primary channel of detector.

With respect to FIG. 4, when alarm is detected, a time counter is started inside the device. This counter can be located in the detector 20-3, or in the control circuits 22 without limitation. At the same time, RCH 20-2 fan starts.

The redundant channel fan 20-2 operates at the same speed of MCH fan 20-1. The RCH fan 20-2 pulls the smoke from the sample point 18-j in the RPN 14. After a transport time Tt (equal to the transport time of the MPN because it is built in the same way) the ASD indicates an alarm on the RCH 20-2, and the time counter is stopped. The time indicator in the counter can be stored in the unit 22d as illustrated in FIG. 5.

Figure 5:
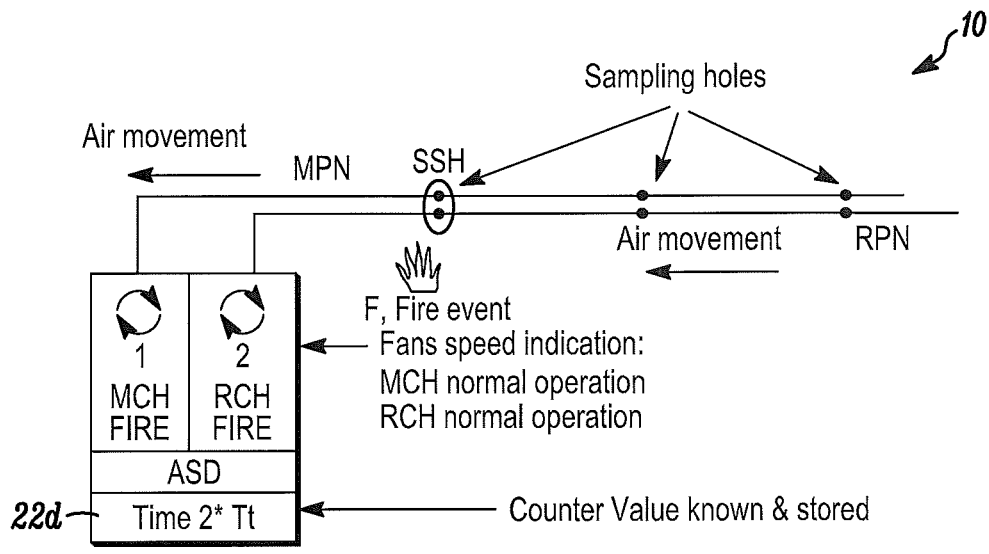
FIG. 5 is a block diagram of the embodiment of FIG. 3 when the fire event is detected by redundant channel of detector.

This time is designated as 2*Tt and the status of the system is illustrated in FIG. 5. From this time measurement, it is possible to determine the location of the SSH, the smoke entry point 18-j, by comparison of measured Tt with the known transport time Ttx of every sample point 18-1, -2 . . . -n where x is a generic hole. This transport time Ttx can be obtained in two ways as below.

Figure 6:
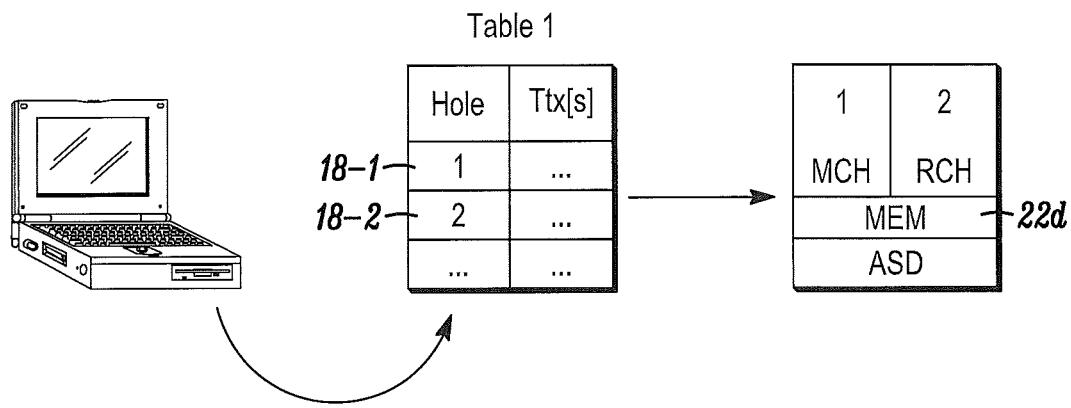
FIG. 6 illustrates aspects of determining smoke transport times.

Considering that this is a fluid-dynamic problem, there could be other solutions, all included in the scope hereof. Relative to FIG. 6, transit times Ttx(s) can be calculated with software, then stored inside the memory, MEM 22d, of the device as Table 1 with an entry for each of the sample points 18-i. In fact, it is sufficient to know the power of the fan (in terms of flow and pressure) and the pipe configuration (in terms of geometry: pipe diameters, hole diameters and distance) to determine the transport time with fluid-dynamics law.

Figure 7:
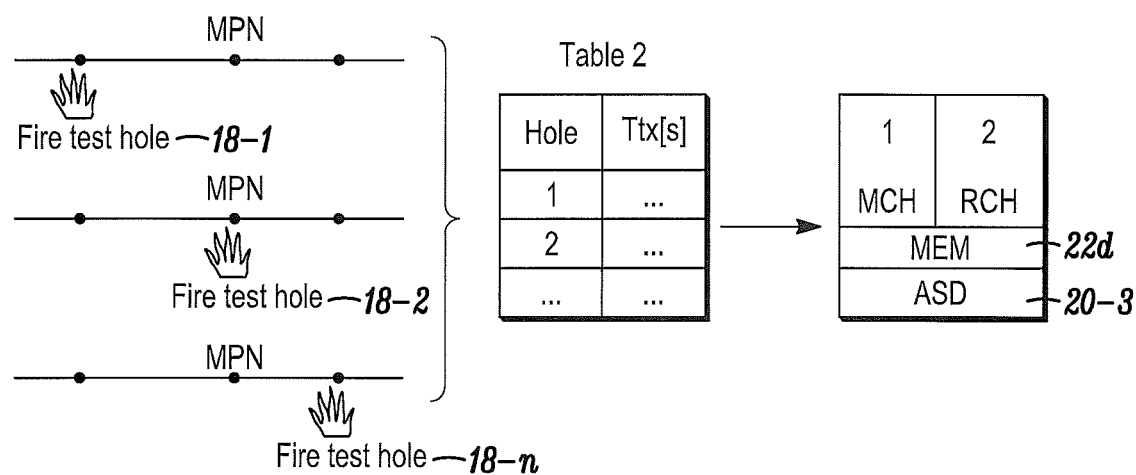
FIG. 7 illustrates additional aspects of determining smoke transport times.

Relative to FIG. 7, a different Table 2 can be obtained from testing activity on site, after the pipe installation. A cotton wick can be burned near every sampling hole, such as 18-1, -2 . . . -n. By triggering the start (when cotton starts to burn) and the end (when alarm is indicated) of this process for every hole, a map of transport time, Table 2, can be obtained for the main pipe network 12 and stored inside the memory, MEM 22d, of the device.

The final indication of the active smoke sample point, such as 18-l, can be displayed to the user in a different number of ways: for example (but not limited to) directly on the device such as at 22c, on a fire panel 24, such as at 24b, connected to the device, or on a computer connected to the device. If the SSH indication is provided in, or on the device, it can be displayed with (but not limited to) bar graph or in a LCD display.

To avoid dust/contamination or blockage in the RPN, it could be useful to automatically and periodically activate the RCH fan 20-2. In this way, airflow will be checked with the standard equipment of ASD. Eventual malfunction of the RPN or RCH fans can be detected and proper maintenance can be ordered. It is a characteristic of this invention that, if the smoke enters more than one sampling hole in the main piping network 12, the related SSH indication will reflect the hole closest to the ASD.

In summary, a redundant pipe system and independent fans are used to first detect a fire condition, and then, establish a transport time by using the redundant pipe system to make a second fire determination. The fans rotate in the same direction. No smoke clearing process is needed.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. An aspirated detector system comprising:
a first ambient air input network which includes a plurality of spaced apart intake points;
a second ambient air input network which includes a second plurality of spaced apart intake points, the first and second networks are substantially identical;
an ambient condition detector coupled to the networks, which includes first and second intake elements configured to draw ambient air from a respective network to the detector, wherein a transport time of a selected condition from an intake point of one network to the detector can be determined by detecting the selected condition with both networks; and
circuitry to actuate one intake element, and, in response to sensing the detected condition at the detector, to actuate the second intake element and a timer to establish the transport time.

2. A system as in claim 1 where the circuitry, in response to sensing the selected condition, at the detector, terminates operation of the timer.

3. A system as in claim 2 where contents of the timer are used to determine the transport time.

4. A system as in claim 3 where contents of the timer are used to determine the transport time.

5. A system as in claim 4 where the intake elements both rotate in a common direction.

6. A system as in claim 4 where the elements are selected from a class which includes, at least, fans, blowers, and aspirators.

7. A system as in claim 4 which includes operating the elements at a common speed.

8. A system as in claim 4 wherein the detector comprises one of a smoke sensor, or a gas sensor.

9. A system as in claim 8 where the detector comprises a multi-channel aspirated smoke sensor.

10. A system as in claim 9 wherein the timer comprises a counter and an associated source of timing pulses.

11. A system as in claim 1 wherein the intake elements rotate only in a common direction when the transport time is being determined.

12. A system as in claim 4 which includes second circuitry to establish a plurality of transport times where each transport time is associated with a predetermined intake point.

13. A system as in claim 5 which includes second circuitry to establish a plurality of transport times where each transport time is associated with a predetermined intake point.

14. An aspirated detecting system comprising:
   a multi-channel aspirated smoke detector with each channel including an air moving element;
   first and second sets of substantially identical air flow pipes where each set defines a plurality of spaced apart inflow ports;
   control circuits to activate a first element and then a second element to establish a transport time associated with at least one inflow port in response to the detector sensing a predetermined ambient condition; and
   where functioning of the sets of pipes can be interchanged.

15. An aspirated detecting system as in claim 14 where the air moving elements are substantially identical, and rotate in a common direction when determining a transport time.

16. An aspirated detecting system as in claim 15 where the control circuits activate the elements successively, and, start a timer when the second element is activated.

17. An aspirated detecting system as in claim 16 which includes a pre-stored table of possible timer values, each of which is associated with a transport time.

18. An aspirated detecting system as in claim 17 which includes a pre-stored table of possible timer values, each of which is associated with a transport time.

19. An aspirated detecting system comprising:
   a multi-channel aspirated smoke detector with each channel including an air moving element, such as a fan;
   first and second sets of substantially identical air flow pipes where each set defines a plurality of spaced apart inflow ports;
   control circuits which activate a first element and then, in response to detected smoke, activate a second element to establish a transport time associated with at least one inflow port in response to the detector sensing a predetermined smoke condition;
   wherein the control circuits include a storage unit which includes pre-stored timer values which are associated with respective transport times from an associated inflow port; and
   where functioning of the sets of pipes can be interchanged.

* * * * *